United States Patent [19]

Fischer et al.

[11] 4,374,966
[45] Feb. 22, 1983

[54] PROCESS FOR THE MANUFACTURE OF VINYL CHLORIDE POLYMERS BY COATING POLYMERIZATION VESSELS

[75] Inventors: Edgar Fischer, Frankfurt am Main; Johannes Brandrup, Wiesbaden; Jürgen Weinlich, Eppstein, all of Fed. Rep. of Germany

[73] Assignee: Hoechst Aktiengesellschaft, Frankfurt am Main, Fed. Rep. of Germany

[21] Appl. No.: 206,960

[22] Filed: Nov. 14, 1980

[30] Foreign Application Priority Data

Nov. 17, 1979 [DE] Fed. Rep. of Germany ....... 2946461

[51] Int. Cl.³ .......................... C08F 2/18; C08F 14/06
[52] U.S. Cl. .................................. 526/62; 526/344.2; 544/99; 544/100; 544/102
[58] Field of Search ................................. 526/62, 204

[56] References Cited

U.S. PATENT DOCUMENTS

| 3,669,946 | 6/1972 | Koyanagi | 526/62 |
| 4,068,059 | 1/1978 | Witenhafer | 526/62 |
| 4,098,972 | 7/1978 | Ogawa | 526/62 |
| 4,105,838 | 8/1978 | Kitamura | 526/62 |
| 4,142,033 | 2/1979 | Witenhafer | 526/62 |
| 4,173,696 | 11/1979 | Koyanagi | 526/62 |

FOREIGN PATENT DOCUMENTS

| 166 | 1/1979 | European Pat. Off. . | |
| 2044259 | 3/1972 | Fed. Rep. of Germany | 526/62 |
| 2632469 | 2/1977 | Fed. Rep. of Germany | 526/62 |
| 2289532 | 5/1976 | France | 526/62 |
| 2305449 | 10/1976 | France | 526/62 |
| 2318898 | 2/1977 | France | 526/62 |

Primary Examiner—C. A. Henderson
Attorney, Agent, or Firm—Curtis, Morris & Safford

[57] ABSTRACT

A process for the manufacture of vinyl chloride polymers by polymerization of the monomer or monomer mixture in a reactor in which the internal walls, and the other parts on which polymer deposits can form, have a covering which contains a representative compound such as depicted by the formula

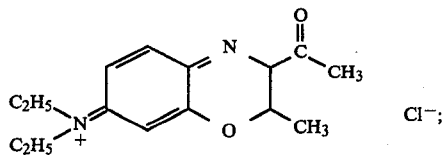

extensive suppression of polymer crusts is thereby obtained.

3 Claims, No Drawings

PROCESS FOR THE MANUFACTURE OF VINYL CHLORIDE POLYMERS BY COATING POLYMERIZATION VESSELS

In the manufacture of vinyl chloride polymers by polymerization in an aqueous medium, polymer crusts form, in the course of the polymerization, on the internal wall of the polymerization autoclaves and on the internal fitments. As a result of these crusts, the polymer yield is reduced and the quality of the product is impaired, because some of the incrustations fall off and pass into the end product and lead to specks or "fish eyes" therein. The crusts furthermore hinder the removal of the heat of polymerization through the reactor walls, whereby uneconomically long reaction times must be accepted.

The removal of such crusts is thus essential and this is usually carried out mechanically. Pressurized-water squirting devices are normally used for this purpose, but they only remove the weakly adhering wall deposits. After every few batches, the reactor must therefore be entered, whilst taking expensive safety precautions, and must be additionally cleaned by hand with the aid of spatulas. This cleaning work is labor-intensive and expensive, causes long stoppage periods and thus considerably reduces the economy of the process.

There has thus been no lack of attempts to reduce or directly to avoid such polymerization crusts in the manufacture of vinyl chloride polymers in aqueous dispersion. However, a universally satisfactory solution to the problem has not yet been found.

Of the numerous known processes, some aim to reduce the crust formation by means of measures relating to process technology. The following examples may be mentioned in this context: stripping the reactor walls with a stirrer designed accordingly, adjusting the wall temperature to at least the temperature of the reaction medium, cooling the reactor wall to $-15°$ C. to $0°$ C., introducing aqueous solutions, for example of salts of permanganic acid, chromic acid or dichromic acid, during the polymerization at the interface between the liquid and the gas phase, polymerization whilst passing an electric current through the liquid reaction medium, and the like.

In other known processes, the components of the polymerization formulation are changed and/or further substances are added to the polymerization liquor.

For the purpose of crust suppression, other known processes use reactors with specially designed or coated internal walls, for example those with a peak-to-valley height of the wall of less than 10 $\mu$m, together with water-soluble, reducing inorganic salts and determined stirring speeds; or an insoluble wall coating consisting of a crosslinked polymeric material which contains polar groups and was manufactured using an aldehyde as the crosslinking component; or a wall covering predominantly consisting of polyethyleneimine which was cured with a urea, aldehyde or diisocyanate, it also being possible for a divalent tin salt of an inorganic acid to be added to the polymerization medium as an inhibitor. Furthermore, wall coatings containing polyaromatic amines or special benzothiazol-2-one hydrazone derivatives have also been described.

German Offenlegungsschrift No. 2,044,259, which teaches, inter alia, the use of organic dyestuffs as crust suppressants, should also be mentioned in this context. In addition to a large number of other representatives, oxazine dyestuffs are also mentioned here in a very general way. However, concrete representatives of this extensive class of dyestuffs are not disclosed either in the description or in the examples.

Finally, it was already known from European Pat. No. 0,000,166 to apply, to the reactor walls, dyestuffs with solubilizing groups, such as —COOH or —SO$_3$H groups, as such or as salts, from aqueous solution, for the purpose of crust suppression. In the same patent application, water-soluble ionic dyestuffs with a heterocyclic ring system are also proposed for this purpose.

The materials known hitherto for crust suppression in vinyl chloride polymerization are in no way fully satisfactory. Thus, for example, they cannot be employed universally and, as a result, they cannot be used for all current PVC types, especially those with a low molecular weight, or, in some cases, the formulations must first be specially made up to suit these substaces. A large number of the active substances must furthermore be employed in an organic solvent, or, because of excessively low effectiveness, solutions with a comparatively high content of, for example, more than 0.1% must be used in order to achieve a satisfactory action. In addition, many of these substances also exhibit an undesired retarding action on the polymerization. To avoid this disadvantage, it is necessary to rinse carefully after the wall treatment with these substances, in order to prevent the excess anti-crust reagent from influencing the polymerization. A requirement resulting therefrom is a high wall affinity of the particular substance, so that there is still sufficient activity on the wall despite careful rinsing.

The object of the present invention was therefore to provide a process for the manufacture of vinyl chloride polymers, which does not have the disadvantages of the state of the art, or which, with combined consideration of the above points, exhibits advantages compared with the known processes, and in which, in particular, crust-preventing substances are employed which exhibit a high and long-lasting crust-preventing action and are also sufficiently active in the copolymerization of vinyl chloride.

This object is achieved, according to the invention, by carrying out the polymerization in a reactor, the internal parts and internal fitments of which are partially or totally provided with a covering which consists of particular water-soluble oxazine dyestuffs.

The present invention thus relates to a process for the manufacture of vinyl chloride homopolymers, copolymers or graft polymers which contain at least 50% by weight of polymerized vinyl chloride units, by polymerization of the monomer or monomer mixture in aqueous dispersion with radical-forming catalysts, suspension stabilizers, if appropriate, emulsifiers and further polymerization aids, which process comprises carrying out the polymerization in a reactor of which the internal walls, and the other parts on which polymer deposits can form, are totally or partially provided with a covering which contains compounds of the general formula

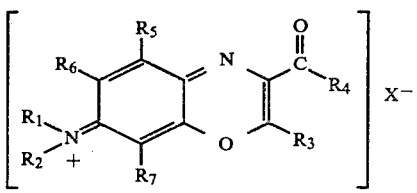

in which the individual substituents have the following meanings:

R$_1$, R$_2$=H; or a saturated hydrocarbon radical with 1–8 C atoms, preferably an aliphatic hydrocarbon radical with 1–6 C atoms;

R$_3$, R$_4$=a saturated hydrocarbon radical with 1–8 C atoms, preferably an aliphatic hydrocarbon radical with 1–6 C atoms; OH; or

in which R'=H or the same as other radicals for R$_1$/R$_2$, and the R"=H or the same as other radicals for R$_1$/R$_2$, or also an aromatic radical, preferably isocyclic with 6 to 10 carbon atoms, which can optionally be substituted by one or more of the following groups: groups corresponding to R$_1$/R$_2$, an O-saturated hydrocarbon radical with 1 to 8 C atoms, OH, COOH,

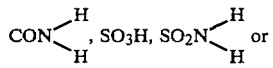

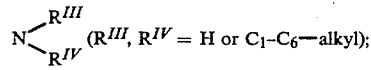

or R$_4$ also=an O-saturated hydrocarbon radical with 1–8 C atoms, preferably an O-aliphatic hydrocarbon radical with 1–6 C atoms; NHOH; or NH—NR'R" (R',R" as above); or R$_3$ and R$_4$=—CH$_2$—CH$_2$—CH$_2$— or

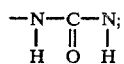

R$_5$, R$_6$, R$_7$=H; a saturated hydrocarbon radical with 1–8 C-atoms, preferably an aliphatic hydrocarbon radical with 1–6 C atoms; or an O-saturated hydrocarbon radical with 1–8 C atoms, preferably an O-aliphatic hydrocarbon radical with 1–6 C atoms; or also R$_5$ and R$_6$=an isocyclic or heterocyclic aromatic radical with 6 to 10 C atoms, optionally substituted by radicals such as R$_1$/R$_2$; and X=any desired monovalent anion or a corresponding anion equivalent.

Furthermore, the invention relates to a polymerization vessel of which the internal walls, and other parts on which polymerization deposits can form, are totally or partially covered with the above coating system.

Finally, a further subject of the present invention consists of the actual compounds of the above general formula and also crust-preventing substances which contain the above compounds.

The anion X$^-$ is not decisive as regards the activity of the substances according to the invention and can therefore be of any desired nature. The following may be mentioned only as examples of these anions: halogen$^-$, preferably Cl$^-$ and Br$^-$, OH$^-$, (SO$_4$$^{--}$)$_{\frac{1}{2}}$, NO$_3$$^-$, (PO$_4$$^{---}$)$_{\frac{1}{3}}$, R'''—COO$^-$ (R'''=C$_{1-5}$-alkyl or aryl), R$^{IV}$—SO$_3$$^-$

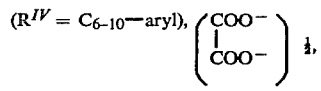

and the like.

In the above general formula, the following meanings are preferred: R$_1$, R$_2$=C$_1$–C$_6$-alkyl, such as methyl, ethyl, propyl, n-butyl, i-butyl or n-hexyl; R$_3$=OH; or C$_1$–C$_6$-alkyl, such as methyl, ethyl, propyl, n-butyl, i-butyl or n-hexyl, especially methyl;

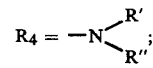

OH; C$_1$–C$_6$-alkyl, such as methyl, ethyl, propyl, n-butyl, i-butyl or n-hexyl; or C$_1$–C$_6$-oxyalkyl; R'=H; or C$_{1-6}$-alkyl, such as methyl, ethyl, propyl, butyl, i-butyl or n-hexyl; R"=H; or C$_{1-6}$-alkyl, such as methyl, ethyl, propyl, n-butyl, i-butyl or n-hexyl; or R$_3$ and R$_4$=—CH$_2$—CH$_2$—CH$_2$—; and R$_5$, R$_6$, R$_7$=H.

Some typical representatives of compounds of the above general formula are listed in the following Table I:

TABLE I

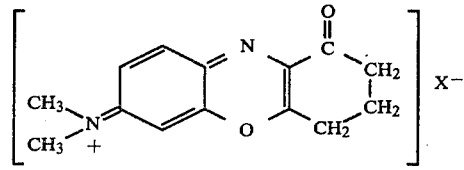

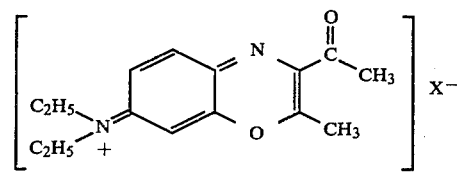

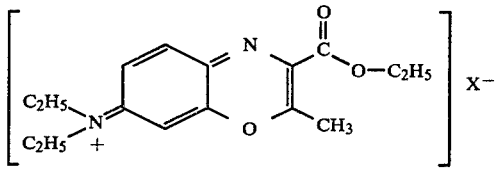

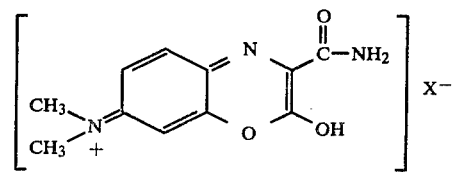

TABLE I-continued

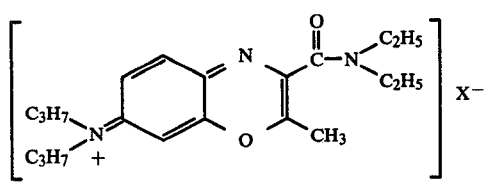

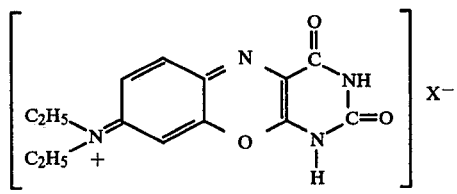

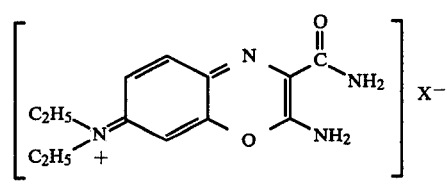

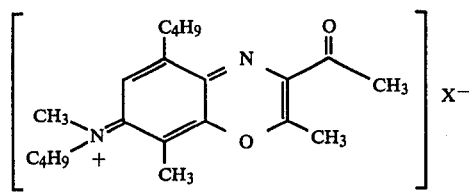

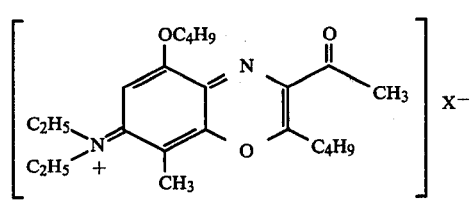

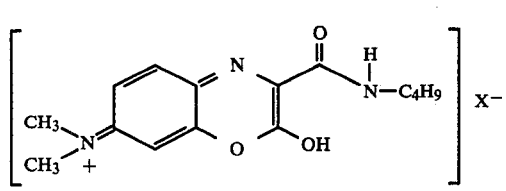

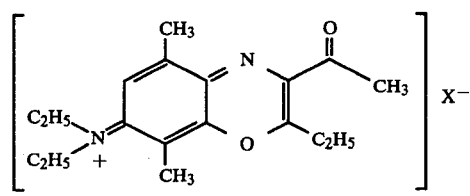

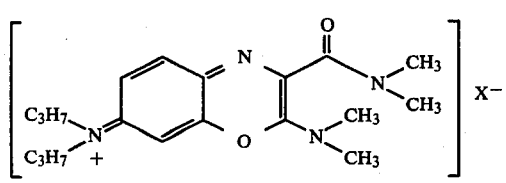

TABLE I-continued

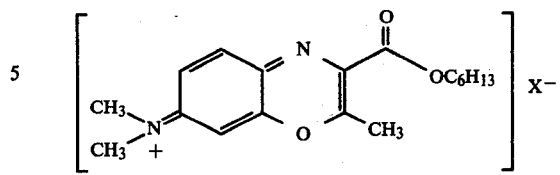

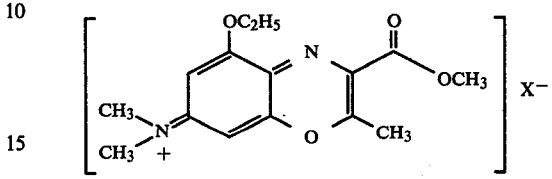

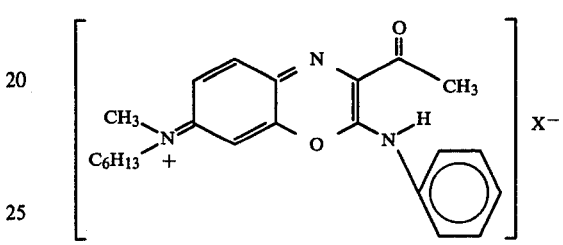

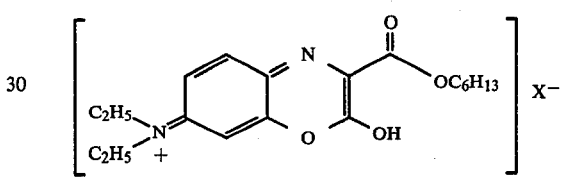

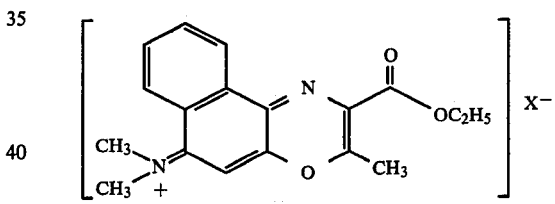

The compounds employed in Examples 3 and 5 are particularly preferred.

Of course, it also lies within the scope of the invention to employ the substances defined above in a mixture with one another.

Moreover, it is possible to combine the substances according to the invention with known crust-suppressing materials, for example with compounds containing azine or thiazine rings, such as methylene blue, organic dyestuffs, such as nigrosine black or aniline black, inorganic pigments, such as described in German Offenlegungsschrift No. 2,044,259, or with polymeric imines according to German Offenlegungsschrift No. 2,357,867, or with polyaromatic amines, such as disclosed in German Offenlegungsschrift No. 2,541,010. The benzothiazol-2-one hydrazone derivatives according to German Offenlegungsschrift No. 2,703,280 and German Offenlegungsschrift No. 2,757,924, and the oxazine and thiazine dyestuffs according to German Offenlegungsschrift No. 2,919,258 and German Offenlegungsschrift No. 2,919,197, respectively, are also suitable for this purpose.

Furthermore, the substances according to the invention can be employed in combination with halides, hydroxides, oxides and carboxylates of any metallic element according to German Offenlegungsschrift No. 2,557,788, in particular with tin-II salts, it being possible, if appropriate, for complexes to form in situ between the substance according to the invention and the additive. Under certain circumstances, such metal complexes of the substance according to the invention, for example with copper, silver, zinc, tin, molybdenum, iron, cobalt or nickel ions, can also be employed directly from the outset, as described in German Offenlegungsschrift No. 2,548,424.

Finally, other possible additives are, inter alia, antifoam agents, antioxidants, wetting agents and the like.

The additives described above are employed in particular when a crosslinking substance or mixture of crosslinking substances is used as the carrier material, because particularly effective fixing to the coating surfaces then results.

The expression "covering" is to be understood as meaning generally those coatings or films and surface coverings which are formed by bringing a solution or dispersion of the substances according to the invention—if appropriate, in combination with other known crust-suppressing substances or corresponding auxiliary substances according to page 12—into contact with the particular internal parts of the reactor, for example by spraying, rinsing and the like, but also those coatings which can be obtained with the concomitant use of a film-forming, preferably crosslinked carrier substance.

The substance according to the above general formula is advantageously applied in an amount of more than 0.001 g/m² and preferably more than 0.01 g/m², depending on the polymerization type, the formulation, the nature of the reactor wall and the like. The upper limit is primarily determined by economic considerations and, as a rule, is about 0.1 g/m².

Since the compounds according to the invention are capable of electron exchange and are oxidized by atmospheric oxygen or, for example, peroxide initiators, the resulting coverings contain not only the actual compound according to the above formula but also its oxidation products. It can be supposed that the charge-transfer complexes or semi-quinone structures forming on the coated surfaces are essential action carriers.

The fixing of the compounds according to the above general formula to the reactor parts to be coated can be carried out, as mentioned above, by using an additional film-forming, preferably crosslinking, carrier substance, as described in German Offenlegungsschrift No. 2,703,280 and German Offenlegungsschrift No. 2,757,924.

However, because they have a sufficiently strong absorptive power on the corresponding reactor parts, the compounds according to the invention are preferably employed without an additional carrier, that is to say the surfaces to be coated are simply treated with a solution or dispersion of this compound. If appropriate, this treatment can be repeated several times after corresponding intermediate drying and possible warming. As a rule, however, a single treatment is sufficient. This treatment is carried out after the customary processes, in general at normal temperature, for example by rinsing, flushing, coating, spraying with flushing jets, and the like, and this is carried out as a rule before every polymerization batch. It has proved advantageous, in this context, to rinse the treated surfaces, before the polymerization, with approximately the same amount of water or polymerization liquor, and to remove the solutions run off.

In addition to water, suitable solvents for the compounds, according to the invention, for the manufacture of the corresponding treatment solutions are preferably those solvents which are at least partially soluble in water (or are at least partially miscible with water), for example lower alcohols, such as methanol, ethanol, n(i)-propanol and n(i)-butanol, ether-alcohols, such as glycol monomethyl ether, ketones, such as acetone, esters, such as ethyl acetate or butyl acetate, dimethylformamide, dimethylacetamide, dimethyl sulfoxide, acetonitrile, or corresponding mixtures with one another or with water.

Preferably, water or its mixtures with lower alcohols having 1-3 C atoms are employed, especially water/methanol mixtures, it being possible for the water content of these mixtures to be more than 50% by weight, relative to the total mixture, depending on the solubility (which naturally depends on the nature of the substituents) and the desired concentration. Substances which carry acid or basic groups can also be transferred into aqueous or aqueous/alcoholic solution by salt formation at the corresponding pH value. Those compounds which become soluble at a pH value of more than 7, preferably of between 8 and 10.5, are particularly suitable. In the strongly acid range, the activity of the substances is sometimes considerably reduced.

The content of substance according to the invention in the solutions to be used can vary within wide limits, approximately between 0.1 mole and 100 mmoles per liter. Even the highly dilute solutions have a low sensitivity towards oxidation by atmospheric oxygen and do not require extensively anaerobic operation. Solutions containing 1-50 mmoles of substance/liter are preferred; these can be handled and used under normal conditions, that is to say in air.

The treatment solutions used for this process possess a marked reducing power, especially in the alkaline range. Partially oxidized solutions show no impairment of their action. The charge-transfer complexes probably contained therein can even exhibit an increase in action. It is not therefore necessary for the solutions either to be freshly prepared or to be manufactured and stored under nitrogen protection. The substances claimed can also be employed in reduced form, for example reduced with dithionite or formamidine-sulfinic acid; some of these solutions are particularly economical in use and their action is enhanced.

In order to improve the wetting properties of the solutions to be used, it is advantageously possible to add thereto the same dispersing agents or wetting agents which are also added to the liquor for the suspension polymerization; examples of this are described in German Offenlegungsschrift No. 2,703,280 or German Offenlegungsschrift No. 2,735,770.

Any polymerization vessel for the polymerization of ethylenically unsaturated compounds can be provided with the covering according to the invention, if appropriate with the concomitant use, in the case of non-metallic reactors, of carrier substances (lacquers) for fixing purposes. The surfaces to be coated can thus consist of the most diverse materials, for example glass, enamel or metal, preferably steel. The greatest problems regarding polymer deposition generally occur in steel reactors, whereupon these are preferably considered for the covering according to the invention.

Polymer deposits can form not only on the internal walls of the polymerization reactor but also on the so-called internal fitments, such as stirring devices, flow deflectors (baffles), charging nozzles, valves, pumps, piping, measuring instruments and internal coolers (heat exchangers), which are therefore likewise to be totally or partially coated or treated. The same applies to external coolers insofar as they are more or less directly mounted on the polymerization vessel. If appropriate, it can also be advantageous to add small amounts of the crust-suppressing substance according to the invention, for example 50-100 ppm, to the polymerization liquor.

In the process, according to the invention, for the manufacture of vinyl chloride polymers, the polymerization itself is carried out in accordance with customary methods, it being possible for vinyl chloride homopolymers, graft copolymers or copolymers to be manufactured, using the continuous or discontinuous procedure, with or without the use of a seed prepolymer or the like. In this process, polymerization can be carried out in aqueous dispersion, that is to say in emulsion or suspension, in the presence of the customary initiators, emulsifiers or suspension stabilizers and, if appropriate, other polymerization aids. The polymerization process can be carried out with cooling under reflux and furthermore also using the filled reactor procedure, in which the reaction vessel is completely filled with the polymerization medium and is kept in this state throughout the entire polymerization by metering in further amounts accordingly.

The following may be mentioned as examples of initiators, which are advantageously employed in amounts of 0.01 to 3% by weight, preferably 0.1-0.3% by weight, relative to the monomer: diaryl and diacyl peroxides, such as diacetyl, acetyl benzoyl, dilauroyl, dibenzoyl, bis-2,4-dichlorobenzoyl and bis-2-methylbenzoyl peroxide; dialkyl peroxides, such as di-tert.-butyl peroxide; peresters, such as tert.-butyl percarbonate, tert.-butyl peracetate, tert.-butyl peroctoate and tert.-butyl perpivalate; dialkyl peroxydicarbonates, such as diisopropyl, diethylhexyl, dicyclohexyl and diethylcyclohexyl peroxydicarbonates; mixed anhydrides of organic sulfoperacids or organic acids, such as acetyl cyclohexylsulfonyl peroxide; azo compounds known as polymerization catalysts, such as azo-isobutyronitrile; and also persulfates, such as potassium, sodium or ammonium persulfates; hydrogen peroxide, tert.-butyl hydroperoxide or other water-soluble peroxides, and also corresponding mixtures. In the case of peroxide catalysts, these can also be employed in the presence of 0.01-1% by weight, relative to the monomer, of one or more reducing substances which are suitable for forming a redox catalyst system, such as, for example, sulfites, bisulfites, dithionites, thiosulfates and aldehyde sulfoxylates, for example formaldehyde sulfoxylate. If appropriate, the polymerization can be carried out in the presence of soluble metal salts, for example copper, silver, iron or chromium salts, the amounts advantageously being 0.05-10 ppm (based on the metal and relative to the monomer).

Furthermore, in the case where it is carried out in accordance with the suspension process, the polymerization can take place in the presence of 0.01-1% by weight, preferably 0.05-0.3% by weight, relative to the monomer, of one (or more) protective colloids, such as, for example, polyvinyl alcohol which also optionally contains up to 40 mole % of acetyl groups, cellulose derivatives, such as water-soluble methylcellulose, carboxymethylcellulose, hydroxyethylcellulose and methylhydroxypropylcellulose, and gelatin, glue and dextran, and also copolymers of maleic acid or its half-esters and styrenes.

Furthermore, the polymerization can be carried out in the presence of 0.01-5% by weight, relative to the monomer, of one or more emulsifiers, it also being possible for the emulsifiers to be employed in a mixture with the abovementioned protective colloids. The emulsifiers used can be anionic, amphoteric, cationic or non-ionic. Examples of suitable anionic emulsifiers are: alkali metal, alkaine earth metal and ammonium salts of fatty acids, such as lauric, palmitic or stearic acid; of acid fatty alcohol sulfates; of paraffinsulfonic acids; of alkylarylsulfonic acids, such as dodecylbenzenesulfonic or dibutylnaphthalenesulfonic acid; and of dialkyl sulfosuccinates; and also the alkali metal and ammonium salts of fatty acids containing epoxy groups, such as epoxystearic acid; and of reaction products of peracids, for example peracetic acid, with saturated fatty acids, such as oleic acid. Examples of suitable amphoteric and cationic emulsifiers are: alkylbetaines, such as dodecylbetaine, and alkylpyridinium salts, such as laurylpyridinium hydrochloride; and also alkylammonium salts, such as hydroxyethyldodecylammonium chloride. Examples of possible non-ionic emulsifiers are: partial fatty acid esters of polyhydric alcohols, such as glycerol monostearate and sorbitol monolaurate, monooleate or monopalmitate; polyoxyethylene ethers of fatty alcohols or of aromatic hydroxyl compounds; polyoxyethylene esters of fatty acids, and also polypropylene oxide/polyethylene oxide condensation products.

In addition to catalysts and, if appropriate, protective colloids and/or emulsifiers, the polymerization can be carried out in the presence of buffer substances, such as, for example, alkali metal acetates, borax, alkali metal phosphates, alkali metal carbonates, ammonia or ammonium salts of carboxylic acids, and also in the presence of molecular size regulators, such as, for example, aliphatic aldehydes with 2-4 carbon atoms, chlorohydrocarbons or bromohydrocarbons, such as, for example, dichloroethylene and trichloroethylene, chloroform, bromoform and methylene chloride, and also mercaptans.

As a rule, the polymerization temperature is 30°-100° C., the polymerization pressure is 4-40 atmospheres and the pH value is 3.5-8.

One or more of the following monomers are suitable examples of monomers for copolymerization with vinyl chloride: olefins, such as ethylene or propylene; vinyl esters of straight-chain or branched carboxylic acids with 2-20, preferably 2-4 carbon atoms, such as vinyl acetate, propionate, butyrate and 1-ethylhexoate and vinyl isotridecanoate; vinyl halides, such as vinyl fluoride and vinylidene chloride; vinyl ethers; vinylpyridine; unsaturated acids, such as maleic, fumaric, acrylic and methacrylic acid and their monoesters or diesters with monoalcohols or dialcohols having 1-10 carbon atoms; maleic anhydride; maleimide and also its N-substitution products with aromatic, cycloaliphatic and, if appropriate, branched, aliphatic substituents; acrylonitrile, and styrene.

Examples of polymers which can be used for graft copolymerization are elastomeric polymers which have been obtained by the polymerization of one or more of the following monomers: dienes, such as butadiene and cyclopentadiene; olefins, such as ethylene and propylene; styrene; unsaturated acids, such as acrylic or methacrylic acid, and also their esters with monoalcohols or dialcohols having 1-10 carbon atoms; acrylonitrile;

vinyl compounds; such as vinyl esters of straight-chain or branched carboxylic acids with 2-20, preferably 2-4, carbon atoms; and vinyl halides, such as vinyl chloride and vinylidene chloride.

After the polymerization, further substances can be added to the polymers obtained as an aqueous dispersion, in order to stabilize or to improve their properties for further processing. The dry polymer is then obtained after customary preparation techniques.

The process according to the invention can preferably be used for polymerization in aqueous suspension with oil-soluble initiators, at least one protective colloid (suspension stabilizer) being added, and in particular for the manufacture of vinyl chloride homopolymers and also for vinyl chloride copolymers containing at least 50% by weight, preferably 80-99% by weight, of polymerized vinyl chloride units.

The manufacture of the substances according to the invention is carried out analogously to known synthesis routes, the correspondingly substituted starting materials being employed in each case. A general synthesis route for analogous compounds is described in Ber. 25, 1,055-1,067. It starts from a compound of the formula I (see following reaction scheme), which is converted to a compound of the formula II using $HNO_2$. The nitroso compound II is then reacted with a $\beta$-dicarbonyl compound III, and this leads to the substances, according to the invention, with the structure IV:

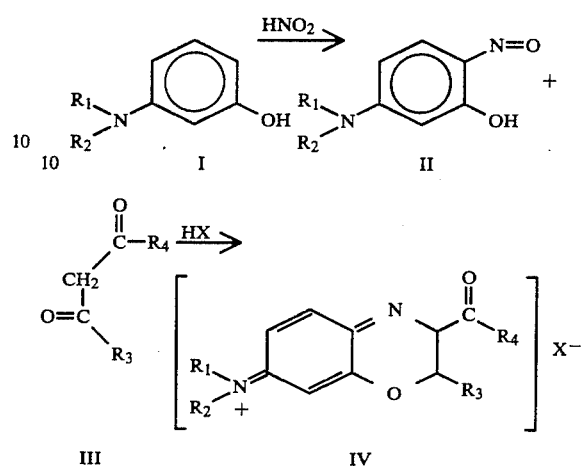

The reaction of I to give II is preferably carried out in water, $C_1$-$C_3$-alcohols, acetic acid or corresponding mixtures, at temperatures which are preferably below 25° C., and especially at 0°-10° C. The reaction of II and III to give IV is advantageously carried out in the same reaction medium as described above, preferably in acetic acid. The temperatures in this case are generally 60° to 150° C., preferably the boiling point of the reaction medium under normal pressure.

If these compounds are employed as crust suppressants, isolation is not necessarily required; rather, the resulting solutions can, for example, be further processed as such, that is to say dilute, and provided with further additives.

The good crust-suppressing and low polymerization-inhibiting action of the oxazine derivatives according to the invention is to be regarded as surprising because—as will be shown by means of comparison experiments below—a large number of representatives of the oxazines are either inactive or some of them even exhibit crust-promoting properties, and in some cases they additionally act as polymerization inhibitors.

Furthermore, it is unexpected and surprising that the use of the substances claimed does not lead to a reduction in the particle size distribution spectrum of the polymer, required by the formulation, so that frequently tiresome and expensive special adaptation of the polymerization formulation to the crust-preventing process is not necessary. In contrast, it has even been found that, on using the compounds according to the invention, certain product properties are markedly influenced in the beneficial sense, such as the ZFR value characterizing the plasticizer uptake (DIN 53,417, page 1).

A further advantage of the present process is the wide range of application, even for the inherently problematic product types with a low molecular weight.

Because of the high wall affinity of the oxazine derivatives according to the invention, they can be employed in very low concentrations, and this has advantages compared with the hitherto known representatives of this class of substance, inter alia also because of the low level of environmental pollution caused thereby and the easier treatment of the effluent. In this respect, it was found that concentrations as low as 0.005% of active substance in the treatment solution has a usable effect, but concentrations of 0.01-0.25% will generally be preferred.

The process according to the invention also makes it possible to carry out many polymerization batches over long periods of time without troublesome crust formation on the walls and the internal fitments of the reactor. This ensures constantly good heat transfer onto the container wall, which heat transfer is virtually unimpaired by the covering layer, and hence ensures uniform product quality. Time-consuming, capacity-reducing wall-cleaning operations are dispensed with and the same applies to the otherwise unavoidable frequent opening of the reactor with the associated harmful vinyl chloride emissions. In continuous polymerization, the periods of time which elapse until the continuous operation is shut down can be increased several fold.

A further advantage of the process according to the invention is that it can also be applied in relatively old reactors with considerable wall roughnesses, which promote crust formation to a particularly great extent, because the nucleating function of these wall pores is effectively suppressed by the covering according to the invention. This applies especially when employing particularly active complex-forming agents of the preferred structure with which coverings of particularly high adhesion and durability can moreover be achieved, which coverings have a good crust-suppressing action, in particular also in the copolymerization of vinyl chloride.

The compounds according to the invention can not only be employed as crust-preventing agents but, as a result of their complex-forming properties, can advantageously also be used in the field of corrosion protection, in electroplating, as depolarizers and for serological tests.

The invention is described in greater detail below with the aid of examples.

EXAMPLES 1 TO 6 AND COMPARISON EXPERIMENTS A TO G

I. Preparation of the oxazine derivatives according to the invention

The preparation is illustrated with the aid of the following compound:

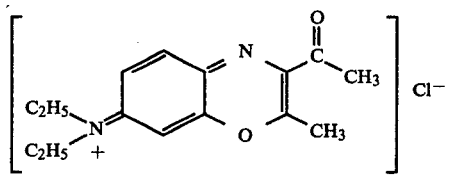

73.64 parts by weight of glacial acetic acid and 5.355 parts by weight of hydrochloric acid of 37.2% strength by weight were initially introduced into the reaction vessel and 7.44 parts by weight of 3-diethylaminophenol were dissolved therein at 20° C. Nitrosation was then carried out at 15°–20° C. with 7.75 parts by weight of $NaNO_2$ solution (40% strength). 4.5 parts by weight of acetylacetone were then introduced and the reaction mixture was boiled under reflux for 3 hours. It is left to cool to room temperature in the course of about 2 hours.

For working-up, the batch was introduced into 80 parts by weight of water and the precipitated product was filtered off, rinsed with 150 parts by weight of $H_2O$, in portions, and dried to constant weight at 60° C. in vacuo.

This synthesis can be applied in a general manner to the compounds claimed, except that, to bring the reaction to completion, the reaction time must under certain circumstances be increased from 3 to up to 10 hours and the working-up and separation of readily soluble compounds must be carried out with sodium chloride solution in place of water, after the boiling under reflux.

II. Use in the polymerization process

The most reliable method for an exact and comparative thorough test consists in treating absolutely identical and identically pretreated metal sheets with the particular substances, and then fixing them in a reactor together with metal sheets which have been pretreated in exactly the same way but prepared without using the test substance, as a blank, in order to carry out the evaluation only after several polymerization operations. The results found must then be related to the values of the corresponding blanks in each case. The following process was carried out in this way:

In a 400 liter $V_4A$ reactor which is equipped with an impeller stirrer, a $V_4A$ sleeve is stretched against the kettle wall in such a way that about 25 polished sample plates, which have a size of 200 mm×36 mm and a peak-to-valley height of about $3\mu$ and are made of the same material as the kettle, can be fixed to the inside of the sleeve. The crust-preventing systems to be tested are applied to these sample plates, by painting on, from their solutions with the indicated content of crust preventor. For each test series, two sample plates treated without the active substance are run at the same time in order to determine the blank value.

The test is carried out as follows:

After the initial introduction of 215 liters of deionized water, which contains 50 g of partially saponified polyvinyl acetate and 40 g of methylhydroxypropylcellulose, in solution, as the dispersing agent, the reactor is closed, the air is displaced, 115 kg of vinyl chloride are then charged in and 115 g of di-2-ethylhexyl peroxydicarbonate (as a 65% strength solution is aliphatic compounds), as the activator, are subsequently introduced under pressure.

The reactor is then heated to 53° C., whilst stirring (150 rpm), and kept at 53° C. until the reactor pressure has fallen by 4.0 bars. The polymerization time is about 6 hours. After the reaction has ended, the reaction mixture is cooled, the polymerization reactor is freed of monomer, emptied, flushed with water and opened.

The sample plates are assessed and crust preventors are applied again. In this same way, three batches are carried out in the reactor. After the three batches, the sample plates are separated from the sleeve and dried and the weight of the crust on the treated surface of the sample plate is determined quantitatively.

The treatment solutions for Examples 1–6 and comparison experiments A to G are of 0.1% strength, relative to the active substance, and consist of 0.1 g of test substance, 10 ml of 2 N NaOH and 90 ml of deionized water.

The test substance is not used in the case of the blank value.

The results are listed in the following Table II and are indicated as test value/blank value. This shows that many oxazine and thiazine dyestuffs have an inadequate crust-preventing action or virtually no such action, such as those according to comparison experiments B to G. Some of them are even markedly poorer than the blank value.

TABLE II

| Example | Formula | Crust (mg) | Remark |
|---|---|---|---|
| A | Blank value | 158 (±5%) | Comparison experiment |
| B | 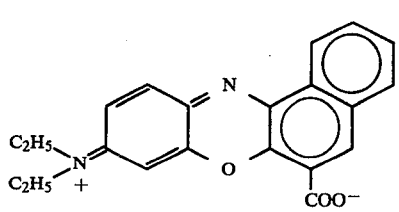 | 160/158 | Comparison experiment |

TABLE II-continued

| Example | Formula | Crust (mg) | Remark |
|---|---|---|---|
| C | [structure: dimethylamino quinone imine linked via O to naphthalene with $SO_3^-$] | 176/158 | Comparison experiment |
| D | [structure: quinone-O-phenol with OH] | 180/158 | Comparison experiment |
| E | [structure: dimethylamino quinone imine-O-naphthalene, $Cl^-$] | 84/158 | Comparison experiment |
| F | [structure: dimethylamino quinone imine-O-benzene with $COO^-$ and two OH], | 106/158 | Comparison experiment |
| G | [structure: bis(dimethylamino) phenoxazine type, $Cl^-$] | 120/158 | Comparison experiment |
| 1 | [structure: diethylamino quinone imine linked to cyclohexanone, $Cl^-$] | 23/158 | According to the invention |
| 2 | [structure: diethylamino quinone imine with -CH(CH$_3$)-C(O)CH$_3$ group, $Cl^-$] | 28/158 | According to the invention |
| 3 | [structure: diethylamino quinone imine with -CH(CH$_3$)-C(O)OC$_2$H$_5$, $Cl^-$] | 10/158 | According to the invention |
| 4 | [structure: dimethylamino quinone imine with -CH(OH)-C(O)NH$_2$, $Cl^-$] | 26/158 | According to the invention |

TABLE II-continued

| Example | Formula | Crust (mg) | Remark |
|---|---|---|---|
| 5 | 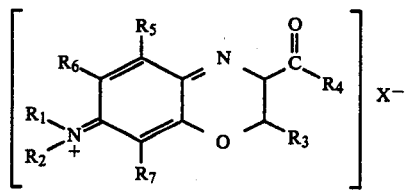 | 19/158 | According to the invention |
| 6 | | 40/158 | According to the invention |

We claim:

1. A process for the manufacture of vinyl chloride homopolymers or copolymers which contain at least 50% by weight of polymerized vinyl chloride units, by polymerization of the monomer or monomer mixture in aqueous dispersion comprising radical-forming catalysts and suspension stabilizers, said process comprises carrying out the polymerization in a reactor of which internal walls thereof, and the other parts thereof on which polymer deposits can form, are provided with a compound of the general formula $$\left[\begin{array}{c}R_5\\R_6\\R_1\\R_2\end{array}\begin{array}{c}N\\+\\R_7\end{array}\begin{array}{c}O\\\parallel\\R_4\\R_3\end{array}\right]X^-$$

in which the individual substituents have the following meanings: $R_1$ to $R_2$ is H or a saturated hydrocarbon radical with 1-8 C-atoms; $R_3$ or $R_4$ is a saturated hydrocarbon radical with 1-8 C-atoms, OH, or

in which R' and R" have the same meaning as for $R_1$ or $R_2$, or denote an aromatic radical with 6 to 10 carbon atoms, or $R_4$ denotes an O-aliphatic hydrocarbon radical with 1-6 C-atoms; or $R_3$ and $R_4$ denote $-CH_2-CH_2-CH_2-$ or

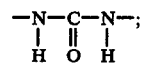

each of $R_5$, $R_6$, $R_7$ denotes H; a saturated hydrocarbon radical with 1-8 C-atoms; or an aliphatic hydrocarbon radical with 1-6 C-atoms; or $R_5$ and $R_6$ is an isocyclic or heterocyclic aromatic radical with 6 to 10 C-atoms; and X is a monovalent anion or a corresponding anion equivalent.

2. A process as claimed in claim 1, wherein $R_1$ and $R_2$ is $C_1-C_6$-alkyl, $R_3$ is $C_1-C_6$-alkyl or OH, $R_4$ is $C_1-C_6$-alkyl, OH or NR'R", in which R' or R" is H or $C_1-C_6$-alkyl, or wherein $R_3$ and $R_4$ is $-CH_2-CH_2-CH_2-$ and $R_5$ to $R_7$ represent H.

3. A process as claimed in claim 1 or 2, which comprises rinsing the coated surfaces with water before the polymerization.

* * * * *